United States Patent
Rossen et al.

(10) Patent No.: US 9,156,815 B2
(45) Date of Patent: Oct. 13, 2015

(54) SALT OF (R)-3-(6-AMINO-PYRIDIN-3-YL)-2-(1-CYCLOHEXYL-1H-IMIDAZOL-4-YL) ETHYL PROPIONATE

(71) Applicant: Sanofi, Paris (FR)

(72) Inventors: Kai Rossen, Frankfurt am Main (DE); Hermut Wehlan, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/359,737

(22) PCT Filed: Nov. 22, 2012

(86) PCT No.: PCT/EP2012/073295
§ 371 (c)(1),
(2) Date: May 21, 2014

(87) PCT Pub. No.: WO2013/076177
PCT Pub. Date: May 30, 2013

(65) Prior Publication Data
US 2014/0336226 A1    Nov. 13, 2014

(30) Foreign Application Priority Data

Nov. 25, 2011   (EP) .................................... 11306560

(51) Int. Cl.
| C07D 401/00 | (2006.01) |
| A61K 31/44 | (2006.01) |
| C07D 401/06 | (2006.01) |
| A61K 31/4439 | (2006.01) |
| C07C 309/35 | (2006.01) |

(52) U.S. Cl.
CPC .......... *C07D 401/06* (2013.01); *A61K 31/4439* (2013.01); *C07C 309/35* (2013.01); *C07B 2200/13* (2013.01)

(58) Field of Classification Search
None
See application file for complete search history.

(56) References Cited

U.S. PATENT DOCUMENTS

2007/0129341 A1*   6/2007   Kallus et al. .................. 514/183

FOREIGN PATENT DOCUMENTS

WO   2005105781 A1   11/2005

OTHER PUBLICATIONS

Morissette, S. et al., Adv. Drug Deliv. Rev. 2004, vol. 56, pp. 275-300.*
Brittain, H., ed., Polymorphism in Pharmaceutical Solids, pp. 318-335.*
Ivanisevic, I., Pharm. Form. Qual. 2011, pp. 30-33.*
Morissette, S. et al. Adv Drug Deliv Rev 2004 vol. 56 pp. 275-300.*
Brittain, H. ed., Polymorphism in Pharmaceutical Solids pp. 318-335 2009.*
Ivanisevic, I. Pharm Form Qual 2011, pp. 30-33.*
Byrn, S., Pfeiffer, R., Ganey, M., Hoiberg, C., Poochikian, G., "Pharmaceutical Solids: A Strategic Approach to Regulatory Considerations"; Pharmaceutical Research, vol. 12, No. 7, 945-954 (Jul. 1995).
Morissette, S., Almarsson, O., Peterson, M. L., Remenar, J. F., Read, M. J., Lemmo, A. V., Ellis, S., Cima, M. J., Gardner, C. R., "High-Throughput Crystallization: Polymorphs, Salts, Co-Crystals and Solvates of Pharmaceutical Solids" Advanced Drug Delivery Reviews, 56(3), 275-300 (Feb. 23, 2004).
European Search Report for European Patent Application No. EP 11 30 6560 dated Feb. 13, 2012.

* cited by examiner

*Primary Examiner* — Heidi Reese
(74) *Attorney, Agent, or Firm* — McDonnell Boehnen Hulbert & Berghoff

(57) ABSTRACT

The invention relates to the salt of naphthalene-1,5-disulfonic acid with (R)-3-(6-amino-pyridin-3-yl)-2-(1-cyclohexyl-1H-imidazol-4-yl)ethyl propionate, which can be represented by the following structural formula of formula (I), to methods for the production thereof, to drugs containing said salt, and to the use of said drugs to treat diseases that are accompanied by thromboses, embolisms, hypercoagulability, or fibrotic changes.

10 Claims, 2 Drawing Sheets

Fig. 1: Measurement of the compound of formula (I), measured in transmission with CuKα₁ radiation at room temperature Raman spectrum of the compound of formula (I) measured in the wavelength range from 3500 to 200 cm$^{-1}$

SALT OF (R)-3-(6-AMINO-PYRIDIN-3-YL)-2-(1-CYCLOHEXYL-1H-IMIDAZOL-4-YL) ETHYL PROPIONATE

This application is a national stage application under 35 U.S.C. §371 of International Application No. PCT/EP2012/073295, filed Nov. 22, 2012, the disclosure of which is explicitly incorporated by reference herein.

Salt of (R)-3-(6-aminopyridin-3)2-(1-cyclohexyl-1H-imidazol-4-yl)propionic acid ethyl ester The invention relates to the salt of naphthalene-1,5-disulfonic acid with (R)-3-(6-aminopyridin-3-yl)-2-(1-cyclohexyl-1H-imidazol-4-yl)propionic acid ethyl ester and the naphthalene-1,5-disulfonic acid salt of (R)-3-(6-aminopyridin-3-yl)-2-(1-cyclohexyl-1H-imidazol-4-yl)propionic acid ethyl ester, which is present in crystalline form or at least in a partially crystalline form, to methods for their production, to drugs containing these compounds, and to the use thereof, where the structure can be represented by the following structural formula of formula (I):

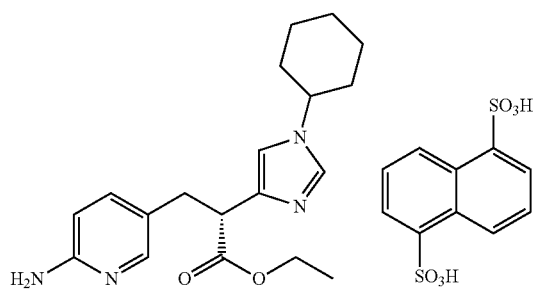

3-(6-Aminopyridin-3-yl)-2-(1-cyclohexyl-1H-imidazol-4-yl)propionic acid ethyl ester hydrochlorides and their pharmacological properties have already been described in the international application PCT/EP2005/003630 (WO2005/105781). The hydrochloride salts of 3-(6-aminopyridin-3-yl)-2-(1-cyclohexyl-1H-imidazol-4-yl)propionic acid ethyl ester or (R)-3-(6-aminopyridin-3-yl)-2-(1-cyclohexyl-1H-imidazol-4-yl)propionic acid ethyl ester have the disadvantage that they are amorphous and cannot be obtained in crystalline form. The above hydrochloride salts can therefore not be purified by crystallization and can therefore not really be used for use as active ingredient in drugs, for which precisely defined degrees of purity of the ingredients are prescribed by the legislator. On account of their physical properties and their handleability, the amorphous hydrochloride salts are also only slightly suited to the galenic production of pharmaceutical preparations such as tablets. Furthermore, (R)-3-(6-aminopyridin-3-yl)-2-(1-cyclohexyl-1H-imidazol-4yl)propionic acid ethyl ester is chemically unstable at elevated temperature and atmospheric humidity. Chemical degradation of the compound occurs and the enantiomeric purity of the chiral compound (R)-3-(6-aminopyridin-3-yl)-2-(1-cyclohexyl-1H-imidazol-4-yl)propionic acid ethyl ester decreases rapidly over time.

An object of the present invention is therefore to provide the compound (R)-3-(6-aminopyridin-3-yl)-2-(1-cyclohexyl-1H-imidazol-4-yl)propionic acid ethyl ester in a suitable form which is easy to purify and has improved stability at elevated temperature and atmospheric humidity.

The present invention thus relates to the salt of naphthalene-1,5-disulfonic acid with (R)-3-(6-aminopyridin-3-yl)-2-(1-cyclohexyl-1H-imidazol-4-yl)propionic acid ethyl ester which can be present in crystalline form or in partially crystalline form. The present invention also relates to the salt of the compound of formula (I)

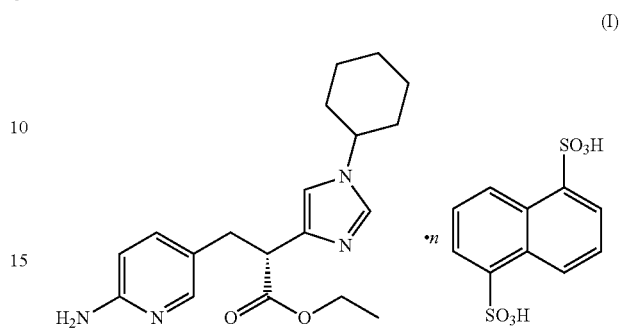

in which n has a value from 0.5 to 1.8 and n indicates the molar ratio of (R)-3-(6-aminopyridin-3-yl)-2-(1-cyclohexyl-1H-imidazol-4-yl)propionic acid ethyl ester to naphthalene-1,5-disulfonic acid.

Preference is given to salts of the compound of formula I in which n has a value from 0.8 to 1.3.

Preference is given to salts of the compound of formula I in which n has a value from 0.95 to 1.05.

The salt according to the invention, in particular the salt of the compound of the formula (I) is at least partially, preferably completely, crystalline. By virtue of the provision of the in particular completely crystalline salts of the compound of formula (I) according to the invention, the active ingredient (R)-3-(6-aminopyridin-3-yl)-2-(1-cyclohexyl-1H-imidazol-4-yl)propionic acid ethyl ester can be purified more easily (e.g. by recrystallization)
have a defined purity required for drug approval
be easily detected and identified by customary methods such as XRPD (X-ray powder diffraction), melting point, IR (infrared spectrum), and it has
a reproducible physical grade
an improved chemical stability and
an improved chiral stability.

Crystalline active ingredients are usually more stable than amorphous ones. As a result, problems with the degradation of the active ingredients and the resulting degradation products are avoided.

The amorphous form of an active ingredient can also comprise an undesired content of solvents. These are generally difficult to remove since recrystallization is not possible. The amorphous form is higher in energy than the crystalline form. This may lead to the random pattern of the molecular distribution of the amorphous form spontaneously rearranging with the release of energy, and some of the energy dissipating. This may lead to a change in the effect of the active ingredient without this being directly visible from a measurable parameter of the active ingredient. A significant influence on the reliability of the active ingredient and thus a risk for patients is the consequence. Only a defined crystalline active ingredient permits a reliable and reproducible formulation with reproducible bioavailability.

A further embodiment of the invention encompasses crystalline salt of formula I, characterized in that the XRPD measured with CuKα radiation at an angular position of 22.48 degrees 2 theta ±0.2 degrees 2 theta has a reflection with high intensity.

A further embodiment of the invention encompasses crystalline salt of formula I, characterized in that the XRPD measured with CuKα radiation at the angular positions has reflections at the following 2 theta values:

7.35 and 22.48 in each case ±0.2 degrees 2 theta.

A further embodiment of the invention encompasses crystalline salt of formula I, characterized in that the XRPD measured with CuKα radiation at the angular positions has reflections at the following 2 theta values:

7.35; 11.4; 13.69; 14.96; 17.49; 19.3 and 22.48 in each case ±0.2 degrees 2 theta.

Selection of the characteristic reflections was made on the basis of the extent of the intensity. An example of an XRPD is shown in FIG. 1.

Depending on the relative atmospheric humidity, the embodiment according to the invention can also comprise a small amount of water; the water content is from about 0.1% to 2.0%. The percentages refer in each case to the weight. This water can be removed as completely as possible from the crystalline salt of formula (I) upon heating to above 100° C. XRPD measurements at different temperatures exhibit essentially unchanged spectra.

Alternatively, the crystalline salts of naphthalene-1,5-disulfonic acid with (R)-3-(6-aminopyridin-3-yl)-2-(1-cyclohexyl-1H-imidazol-4-yl)propionic acid ethyl ester of formula (I) can also be characterized by a Raman spectrum. In this connection, characteristic bands can be determined at the following wavelengths [cm$^{-1}$]: 2936; 1570; 1401; 1352; 998 and 856 in each case ±2 cm$^{-1}$ An example of a Raman spectrum is given in FIG. 2.

The term "polymorphism" is understood as meaning the ability of individual compounds to exist in more than one form or crystalline structure. Different polymorphs are solids which are characterized by the same empirical formula but can have different physical properties.

The term "amorphous" refers to solid compounds which, in the XRPD spectrum at all angular positions, have no reflections which can be clearly delimited from one another in their intensities.

The term "intensity" refers to the amount of measured reflections.

The term "characteristic bands" in the Raman spectrum refers to bands which can be clearly assigned to the crystal form.

Figure 1:
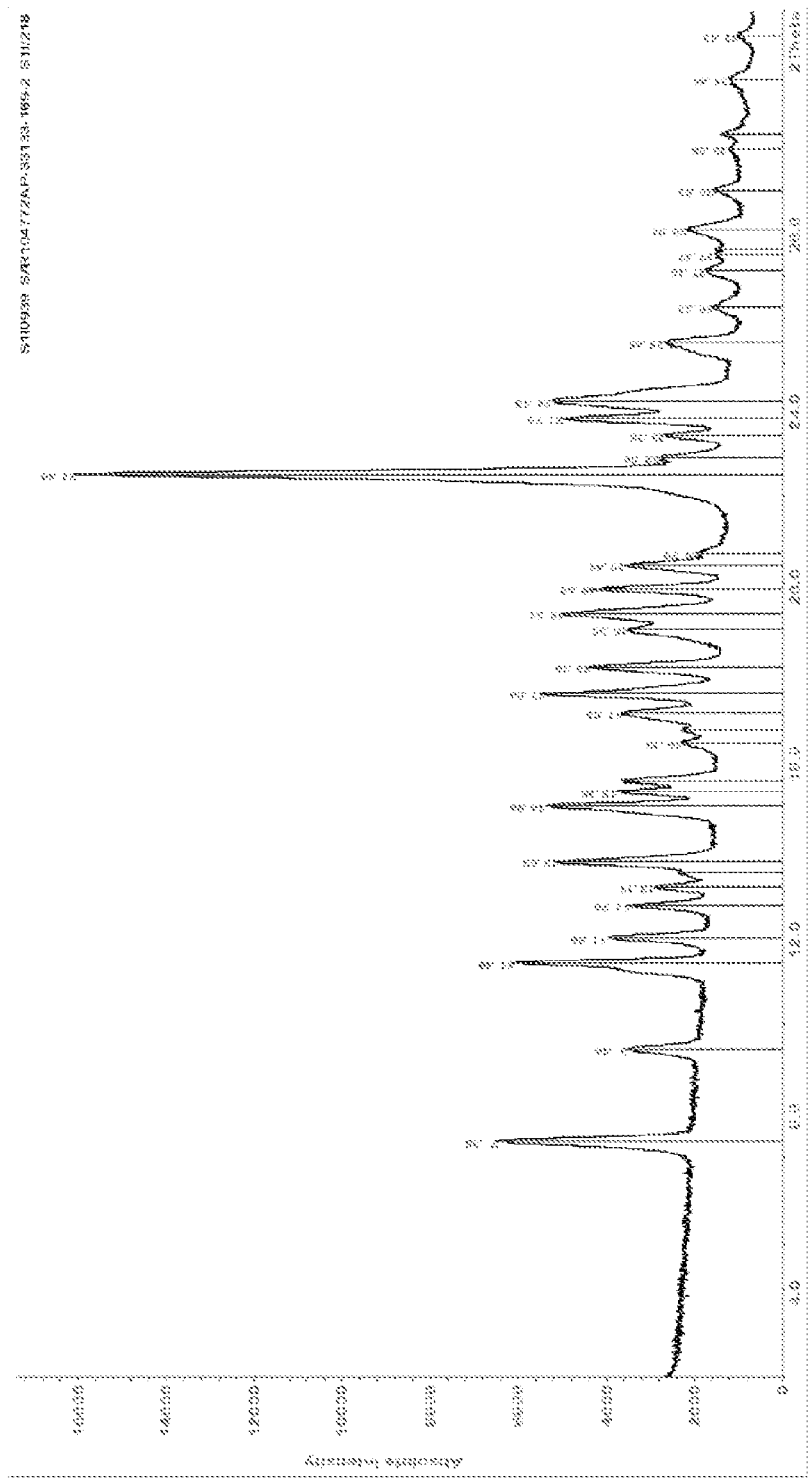
FIG. 1: XRPD spectrum of the crystalline salt of naphthalene-1,5-disulfonic acid with (R)-3-(6-aminopyridin-3-yl)-2-(1-cyclohexyl-1H-imidazol-4-yl)propionic acid ethyl ester of formula (I), measured in transmission with CuKα$_1$ radiation at room temperature (X axis diffraction angle 2 theta (2θ) [°]; Y axis: relative intensity)

The invention furthermore relates to methods for synthesizing the compound of formula (I). A method for the production of the compound of formula (I) is characterized in that naphthalene-1,5-disulfonic acid is dissolved in a solvent A, and a solution of (R)-3-(6-aminopyridin-3-yl)-2-(1-cyclohexyl-1H-imidazol-4-yl)propionic acid ethyl ester in a solvent B is added, then the salt of (R)-3-(6-aminopyridin-3-yl)-2-(1-cyclohexyl-1H-imidazol-4-yl)propionic acid ethyl ester with naphthalene-1,5-disulfonic acid of the formula (I) is obtained. Optionally, the solvents are partially or completely removed. The resulting salt is at least partially, preferably completely, crystalline.

Suitable solvents A are for example polar protic or aprotic solvents such as ethanol, acetone, methyl ethyl ketone, acetonitrile, tetrahydrofuran, dimethyl sulfoxide, dimethylformamide, N-methylpyrrolidinones, methanol, propanol, butanol or water. It is also possible to use mixtures of one or more of the specified solvents.

Suitable solvents B are for example polar protic or aprotic solvents such as ethanol, acetone, methyl ethyl ketone, acetonitrile, tetrahydrofuran, dimethyl sulfoxide, dimethylformamide, N-methylpyrrolidinones, methanol, propanol, butanol or water. It is also possible to use mixtures of one or more of the specified solvents.

The solvents A and B can be the same or different.

The removal of the solvents can take place for example by heating or by passing over or introducing a gas. Suitable gases are for example air, nitrogen or noble gases such as argon or xenon.

The addition of (R)-3-(6-aminopyridin-3-yl)-2-(1-cyclohexyl-1 H-imidazol-4-yl)propionic acid ethyl ester to a solution of naphthalene-1,5-disulfonic acid is advantageous because as a result the possible racemization of (R)-3-(6-aminopyridin-3-yl)-2-(1-cyclohexyl-1H-imidazol-4-yl)propionic acid ethyl ester is largely prevented.

The molar ratio of naphthalene-1,5-disulfonic acid to (R)-3-(6-aminopyridin-3-yl)-2-(1-cyclohexyl-1H-imidazol-4-yl)propionic acid ethyl ester in the method for the production of the compound of formula (I) is from 0.95 to 1.5. A ratio of 1.1 to 1.2 is advantageous.

Suitable temperatures in the method for the production of the compound of formula (I) are from −20° C. to 60° C. or from −10° C. to 25° C. The suitable temperatures depend on the solvent and can easily be ascertained by a person skilled in the art.

The invention also relates to the compound of formula (I) as a drug.

The invention also relates to drugs characterized by a compound of formula (I) together with a pharmaceutically suitable and physiologically compatible carrier.

On account of the pharmacological properties, the compounds according to the invention are suitable for the prophylaxis and treatment of all those disorders which can be treated by inhibiting TAFIa. For example, the compound of formula (I) is suitable both for a prophylactic and also a therapeutic use on humans. They are suitable both for an acute treatment and also for long-term therapy. The compound of formula (I) can be used in patients suffering from wellbeing disorders or illnesses associated with thrombosis, embolisms, hypercoagulability or fibrotic changes. These include myocardial infarction, angina pectoris and all other forms of acute coronary syndrome, stroke, peripheral vascular disorders, deep vein thrombosis, pulmonary embolism, embolic or thrombotic events caused by cardiac arrhythmias, cardiovascular events such as restenosis after revascularization, angioplasty and similar interventions such as stent implants and bypass operations. Furthermore, the compound of formula (I) can be used for all interventions which lead to the blood contacting with foreign surfaces, as in the case of dialysis patients and patients with indwelling catheters. The compound of formula (I) can be used in order to reduce the risk of thrombosis following surgical intervention such as during knee and hip joint operations.

The compound of formula (I) is suitable for the treatment of patients with disseminated intravascular coagulation, sepsis and other intravascular events associated with inflammation. Furthermore, the compound of formula (I) is suitable for the prophylaxis and treatment of patients with atherosclerosis, diabetes and metabolic syndrome and its consequences. Disorders of the hemostatic system (e.g. fibrin deposits) have been implicated in mechanisms which lead to tumor growth and tumor metastasization; the compound of formula (I) is suitable for the slowing or prevention of such processes.

Further indications for the use of the compound of formula (I) are fibrotic changes in the lungs such as chronic obstructive lung disease, adult respiratory distress syndrome (ARDS) and of the eye such as fibrin deposits following eye operations. The compound of formula (I) is also suitable for preventing and/or treating scarring.

The application of the drugs according to the invention can take place by oral, inhalative, rectal or transdermal application or by subcutaneous, intraarticular, intraperitoneal or intravenous injection. Preference is given to oral application. A coating of stents or other surfaces which come into contact with blood in the body with the compound of formula (I) is possible.

The invention also relates to a method for the production of a drug which is characterized in that at least one compound of the formula (I) is converted to a suitable administration form with a pharmaceutically acceptable and physiologically compatible carrier.

For the treatment of the aforementioned diseases, the compound of formula (I) can itself be used as compound, although it is preferably in the form of a pharmaceutical composition with a suitable carrier. The carrier must of course be compatible in the sense that it is compatible with the other constituents of the composition and is not injurious to the health of the patient. The carrier can be a solid or a liquid or both and is preferably formulated with the compound as an individual dose, for example as a tablet, which can contain from 0.05% to 95% by weight of the compound of formula (I). Further pharmaceutically active substances can likewise be present. The pharmaceutical compositions according to the invention can be produced by one of the known pharmaceutical methods, which essentially consist in mixing the constituents with pharmacologically compatible carriers and/or auxiliaries.

Pharmaceutical compositions according to the invention are those which are suitable for oral and peroral (e.g. sublingual) administration, although the most favored method of administration is dependent in each individual case on the nature and severity of the condition to be treated. Sugar-coated formulations and sugar-coated slow-release formulations are also included in the scope of the invention. Acid-resistant and gastric-juice-resistant formulations are possible. Suitable gastric-juice-resistant coatings include cellulose acetate phthalate, poylvinyl acetate phthalate, hydroxypropylmethylcellulose phthalate and anionic polymers of methacrylic acid and methyl methacrylate.

Suitable pharmaceutical compounds for oral administration can be present in separate units, such as for example capsules, cachets, suckable tablets or tablets which each contain a certain amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or shaping a powder or granules of the compound, optionally with one or more additional constituents. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Shaped tablets can be produced by shaping the pulverulent compound wetted with an inert liquid diluent in a suitable machine.

Pharmaceutical compositions which are suitable for peroral (sublingual) administration include suckable tablets which contain a compound according to formula I with a flavoring, usually sucrose, and gum arabic or tragacanth, and pastilles which comprise the compound in an inert base such as gelatin and glycerol or sucrose and gum arabic.

Further suitable solid or galenic preparation forms are for example granules, powders, sugar coated tablets, tablets, (micro)capsules, suppositories, syrups, juices, suspensions, emulsions, drops or injectable solutions, as well as preparations with protracted active ingredient release, in the production of which customary auxiliaries such as carriers, disintegrants, binders, coatings, swelling agents, glidants or lubricants, flavorings, sweeteners and solubility promoters are used. Auxiliaries that are often used include magnesium carbonate, titanium dioxide, lactose, mannitose and other sugars, talc, milk protein, gelatin, starch, cellulose and its derivatives, animal and vegetable oils such as cod liver oil, sunflower oil, peanut oil or sesame oil, polyethylene glycol and solvents such as for example sterile water and mono- or polyhydric alcohols such as glycerol.

Preferably, the pharmaceutical preparations are produced and administered in dosage units, where each unit contains, as active constituent, a certain dose of the compound of formula I according to the invention. For solid dosage units such as tablets, capsules, sugar coated tablets or suppositories, this dose can be up to about 1000 mg, but preferably about 50 to 300 mg, and for injection solutions in ampule form it can be up to about 300 mg, but preferably about 10 to 100 mg.

For the treatment of an adult patient weighing approximately 70 kg, daily doses of about 2 mg to 1000 mg of the compound of formula (I), preferably about 50 mg to 500 mg, are indicated. However, in some circumstances, higher or lower daily doses can be administered. The administration of the daily dose can take place either as a single dose in the form of an individual dosage unit or else two or more smaller dosage units, as well as by multiple administration of subdivided doses at defined intervals.

The compound of formula (I) can be administered either as monotherapy or else in combination or together with anti-thrombotics (anticoagulants and platelet aggregation inhibitors), thrombolytics (plasminogen activators of any kind), other profibrinolytically active substances, blood pressure-reducing drugs, blood sugar regulators, antilipemics and antiarrhythmics.

The production of a number of examples is described in detail below.

EXPERIMENTAL PART

Example 1

Preparation of the crystalline salt of (R)-3-(6-aminopyridin-3-yl)-2-(1-cyclohexyl-1H-imidazol-4-yl) propionic acid ethyl ester with naphthalene-1,5-disulfonic acid 1.50 g (5.20 mmol, 1.2 eq.) of naphthalene-1,5-disulfonic acid are dissolved in 15 mL of water. Where appropriate, some crystals of the compound of formula (I) can also be added. The solution is cooled to 10° C. Then, 1.48 g (4.32 mmol, 1.0 eq.) of (R)-3-(6-aminopyridin-3-yl)-2-(1-cyclohexyl-1H-imidazol-4-yl)-propionic acid ethyl ester (prepared as described in WO2005/105781), which has been dissolved beforehand in 15 mL of acetone/water 2:3, are slowly added dropwise. The solvents are gradually removed by streaming argon over and during which crystals are slowly formed. The argon stream is stopped and the mixture is stirred for 3 hours (h) at room temperature (20° C. to 22° C.). The solids are filtered and dried overnight in the air. This gave a yield of 1.83 g (2.90 mmol, 67%) of the crystalline salt of (R)-3-(6-aminopyridin-3-yl)-2-(1-cyclohexyl-1H-imidazol-4-yl)propionic acid ethyl ester with naphthalene-1,5-disulfonic acid as a white solid.

The resulting crystalline salt of (R)-3-(6-aminopyridin-3-yl)-2-(1-cyclohexyl-1H-imidazol-4-yl)propionic acid ethyl ester with naphthalene-1,5-disulfonic acid exhibits the XRPD shown in FIG. 1. The reflections at the following 2 theta values have the greatest intensities and the relative intensities are shown in brackets:

7.35 (40); 9.43 (21); 11.40 (37); 11.96 (24); 12.70 (21); 13.11 (17); 13.43 (14); 13.69 (31); 14.96 (33); 15.28 (23); 15.53 (22); 16.39 (14); 16.68 (14); 17.05 (22); 17.49 (33); 18.09 (27); 18.95 (21); 19.31 (30); 19.88 (26); 20.40 (22); 20.69 (11); 22.48 (100); 22.85 (17); 23.35 (16); 23.74 (30); 24.14 (32); 25.46 (16); 26.27 (9); 27.09 (10); 27.46 (9); 27.58 (9); 28.03 (13); 28.93 (9); 29.88 (7); 30.20 (8); 31.43 (7); 32.43 (6).

The 2 theta values with the highest intensities are shown in table 1:

TABLE 1

| 2 theta (+/−0.2 degrees 2 theta) | 7.35 | 11.4 | 13.69 | 14.96 | 17.49 | 19.3 | 22.48 |
| --- | --- | --- | --- | --- | --- | --- | --- |

On account of natural differences in the samples or in the measurement method, the 2 theta values of the angular positions can be given with an accuracy of +/−0.2 degrees theta.

The XRPD measurements are carried out in a STOE Stadi-P transmission diffractometer;
Radiation source: CuKα$_1$, λ=1.5406 Å
Angle range: 2° to 40° in 2-theta Bragg
Step width: 0.033° Step time: 1 s At room temperature, linear position-sensitive detectors are used, dry samples are measured in a flat arrangement whereas suspensions are measured in quarz capillaries. The recorded data is processed using WinXPOW V2.12 software.

Raman Spectroscopy

Figure 2:
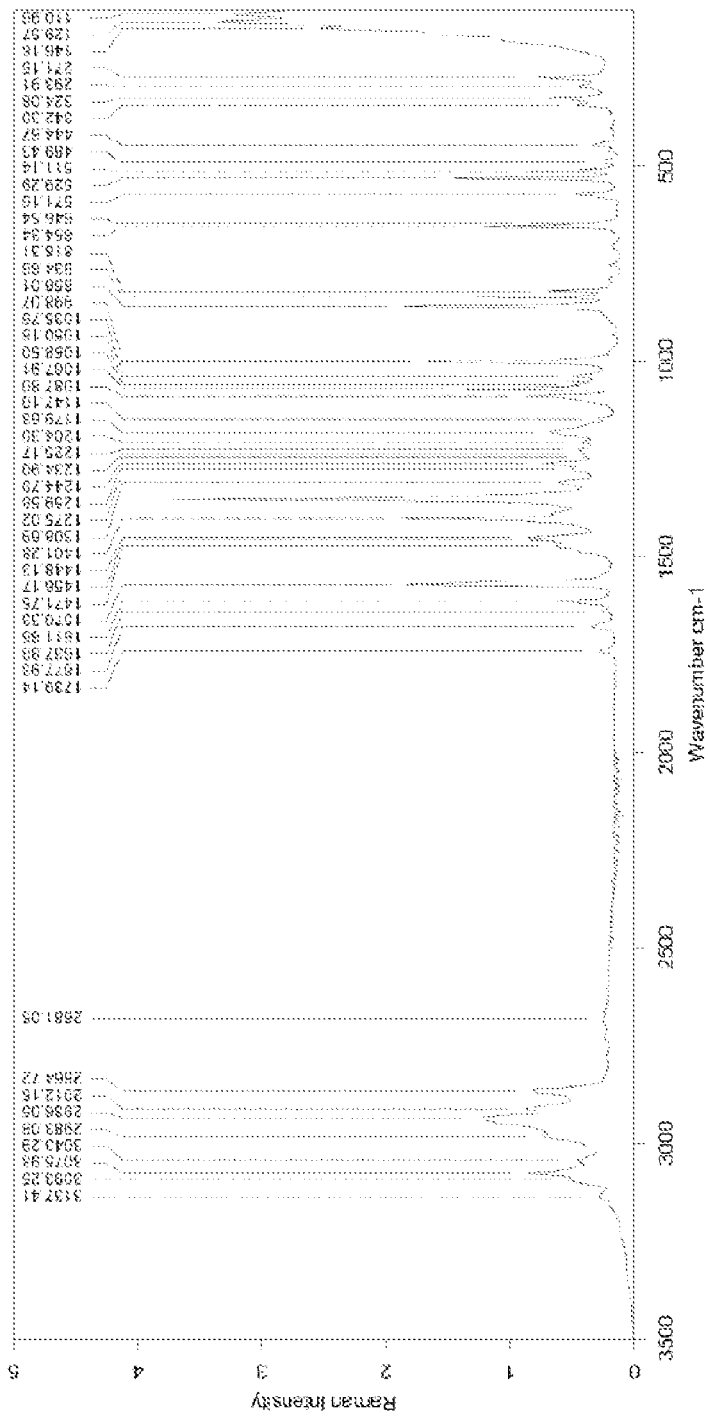
FIG. 2: Raman spectrum of the crystalline salt of naphthalene-1,5-disulfonic acid with (R)-3-(6-aminopyridin-3-yl)-2-(1-cyclohexyl-1H-imidazol-4-yl)propionic acid ethyl ester of formula (I), measured in the wavelength range from 3500 to 200 cm$^{-1}$ (X axis wavelength [cm$^{-1}$]; Y axis: relative intensity)

The Raman spectrum is recorded using an FT-Raman spectrometer (RFS-100/S, BRUKER) equipped with a 1.5W NIR laser (Nd:YAG; λ=1064 nm) and a nitrogen-cooled D418-T NIR detector. The recorded spectrum is processed using OPUS V, 4.2 software. The resulting crystalline salt of (R)-3-(6-aminopyridin-3-yl)-2-(1-cyclohexyl-1H-imidazol-4-yl)propionic acid ethyl ester with naphthalene-1,5-disulfonic acid exhibits the spectrum shown in FIG. 2. Here, characteristic bands can be determined at the following wavelengths [cm$^{-1}$]:

2936; 1570; 1401; 1352; 998 and 856 in each case ±2 cm$^{-1}$

On account of natural differences in the samples or in the measurement method, the characteristic bands at the wavelengths can be stated with an accuracy of +/−2 cm$^{-1}$.

Chiral HPLC: (Chiralcel OD-H/84 (250×4.6 mm), heptane:iPrOH:MeCN 15:1:0.5+0.1% DEA, 30° C., 1 ml/min): R$_t$=27.01 min.

NMR (d6-DMSO, 600 MHz): δ=1.12 (t, 3H), 1.13-1.21 (m, 1H), 1.29-1.39 (m, 2H), 1.57-1.68 (m, 3H), 1.75-1.82 (m, 2H), 1.95-2.02 (m, 2H), 3.02 (dd, 1H), 3.15 (dd, 1H), 4.05-4.15 (m, 2H), 4.17-4.24 (m, 2H), 6.85-6.89 (m, 1H), 7.39-7.44 (m, 2H), 7.68-7.72 (m, 2H), 7.73-7.76 (m, 1H), 7.88-7.99 (m, 4H), 8.86-8.90 (m, 2H), 9.08 (s, 1H).

Example 2

Salt Screening 100 mg of the compound (R)-3-(6-aminopyridin-3-yl)-2-(1-cyclohexyl-1H-imidazol-4-yl)propionic acid ethyl ester (referred to hereinbelow as API) prepared as described in WO2005/105781 are dissolved in 10 mL of acetone in an ultrasound bath at room temperature. The molar ratio between the H$^+$ concentration of the acid and of the API is 2 (for details see table 2). In each cavity of the microtiter plate, 68 microliters of the dissolved API are mixed with 40 microliters of the 0.1 normal acid solutions.

TABLE 2

| Acid | Molecular weight | H+ eq. | Mass [g] in 100 mL solution | Solvent | Molarity of the acid [mol/L] | Molarity of H$^+$ [mol/L] |
| --- | --- | --- | --- | --- | --- | --- |
| Adipic acid | 146.14 | 2 | 0.731 | Ethanol | 0.05 | 0.1 |
| Benzoic acid | 122.12 | 1 | 1.221 | Ethanol | 0.1 | 0.1 |
| Succinic acid | 118.09 | 2 | 0.590 | Water:ethanol 1:1 | 0.05 | 0.1 |
| Citric acid | 192.13 | 2 | 0.961 | Water:ethanol 1:1 | 0.05 | 0.1 |
| Acetic acid | 60.05 | 1 | 0.601 | Ethanol | 0.1 | 0.1 |
| Fumaric acid | 116.08 | 2 | 0.580 | Methanol | 0.05 | 0.1 |
| Glucuronic acid | 194.14 | 1 | 1.941 | Water:ethanol 3:1 | 0.1 | 0.1 |
| Tartaric acid | 150.09 | 2 | 0.750 | Water:ethanol 1:1 | 0.05 | 0.1 |
| Phosphoric acid | 98.00 | 1 | 0.980 | Ethanol | 0.1 | 0.1 |
| Malonic acid | 104.06 | 2 | 0.520 | Water:ethanol 1:1 | 0.05 | 0.1 |
| Hydrochloric acid | 36.46 | 1 | 0.365 | Ethanol | 0.1 | 0.1 |
| Sulfuric acid | 98.08 | 2 | 0.490 | Ethanol | 0.05 | 0.1 | eq. means equivalents

Experimental Procedure:

68 microliters of the dissolved API are pipetted into each cavity of a 96 microtiter plate. Then, in each case 40 microliters of the acids dissolved as in table 2 are added according to the scheme as detailed in table 3. The microtiter plate is shaken at room temperature for 20 min so that an equilibrium is formed in the cavities. Evaporation of the solvents at room temperature in a stream of nitrogen for 2 hours. Then, in each case 40 microliters of the solvents according to the scheme as detailed in table 3 are added. The microtiter plate is shaken at room temperature for 20 min so that an equilibrium is formed in the cavities. Evaporation of the solvent then takes place at room temperature in a stream of nitrogen for 2 hours. Finally, XRPD measurement is carried out. The results are shown in table 3.

TABLE 3

|  | Water | Water:methanol 1:1 | Methanol | Ethanol | 2-Propanol | 2-Methyl-1-propanol | Methyl ethyl ketone | Butyl acetate |
|---|---|---|---|---|---|---|---|---|
| Hydrochloric acid | NKP | NKP | NKP | NKP | NKP | NKP | NKP | NKP |
| Sulfuric acid | NKP | NKP | NKP | NKP | NKP | NKP | NKP | NKP |
| Phosphoric acid | NKP | NKP | NKP | NKP | NKP | NKP | NKP | NKP |
| Acetic acid | NKP | NKP | NKP | NKP | NKP | NKP | NKP | NKP |
| Tartaric acid | NKP | NKP | NKP | NKP | NKP | NKP | NKP | NKP |
| Citric acid | NKP | NKP | NKP | NKP | NKP | NKP | NKP | NKP |
| Fumaric acid | NKP | NKP | NKP | NKP | NKP | NKP | NKP | NKP |
| Succinic acid | NKP | NKP | NKP | KFA | KFA | KFA | NKP | KFA |
| Malonic acid | NKP | NKP | NKP | NKP | NKP | NKP | NKP | NKP |
| Adipic acid | KFA | NKP | KFA | KFA | KFA | KFA | KFA | KFA |
| Benzoic acid | KFA | NKP | KFA | KFA | KFA | KFA | KFA | KFA |
| Glucuronic acid | NKP | NKP | NKP | NKP | NKP | NKP | NKP | NKP |

NKP means no crystalline phase
KFA means free acid crystallizes

The results show that no crystalline salt of (R)-3-(6-aminopyridin-3-yl)-2-(1-cyclohexyl-1H-imidazol-4-yl)propionic acid ethyl ester was found with the tested acids and solvents and it is therefore very difficult to find a solid crystalline salt of (R)-3-(6-aminopyridin-3-yl)-2-(1-cyclohexyl-1H-imidazol-4-yl)propionic acid ethyl ester.

Example 3

Physical Stability

Representative samples of the crystalline salt of (R)-3-(6-aminopyridin-3-yl)-2-(1-cyclohexyl-1H-imidazol-4-yl)propionic acid ethyl ester with naphthalene-1,5-disulfonic acid prepared as in example 1 are stored for 14 days under the conditions (A), (B), (C) and (D):
 (A) 50° C.
 (B) 50° C. and 80% relative atmospheric humidity
 (C) 80° C.
 (D) 80° C. and 80% relative atmospheric humidity Results:

The XRPD measurements at the start and after 14 days are close together. Only a slight loss in mass during the thermogravimetric measurements (apparatus TA Instruments: TGA Q500, atmospheric nitrogen; rate 10° C./min) is observed, which is attributed to the release of water from the crystals. The mass loss is between 1.01% and 1.43%.

Example 4

Chiral Stability

Representative samples of the crystalline salt of (R)-3-(6-aminopyridin-3-yl)-2-(1-cyclohexyl-1H-imidazol-4-yl)propionic acid ethyl ester with naphthalene-1,5-disulfonic acid prepared as in example 1 are stored for 14 days under the conditions (A), (B), (C) and (D) described in example 4:

Results:

|  | Storage conditions | | | |
|---|---|---|---|---|
|  | (A) | (B) | (C) | (D) |
| Enantiomeric purity | 98.8% | 98.8% | 99.0% | 96.3% |

The enantiomeric purity of the measured sample at the start of the measurement was 99.0%. Under the storage condition 50° C. (A) and 50° C. and 80% relative atmospheric humidity (B), a slight increase of 0.2% of the (S) enantiomer was observed. Under the storage conditions 80° C. (C), no change was observed. Under the storage condition 80° C. and 80% relative atmospheric humidity (D), an increase of 2.7% of the (S) enantiomer was observed.

The measurements were carried out using chromatography on chiral phase as described in example 1.

Chiral HPLC: (Chiralcel OD-H/84 (250×4.6 mm), heptane:Isopropanol:Acetonitrile 15:1:0.5+0.1% diethylamine (DEA), 30° C., 1 ml/min): $R_t$=27.01 min.

What is claimed:
1. A salt of formula (I)

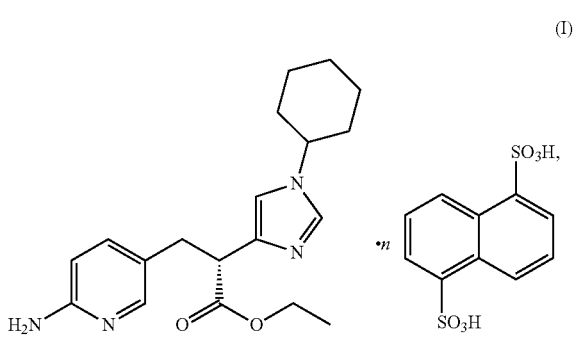 [SMILES: CCOC(=O)[C@H](Cc1ccc(N)nc1)c1cn(C2CCCCC2)cn1 ; O=S(=O)(O)c1cccc2c(S(=O)(=O)O)cccc12]

wherein n has a value from 0.5 to 1.8 and indicates the molar ratio of (R)-3-(6-aminopyridin-3-yl)-2-(1-cyclohexyl-1H-imidazol-4-yl)propionic acid ethyl ester to naphthalene-1,5-disulfonic acid, wherein the salt of formula (I) exhibits an XRPD measured with CuKα radiation at the angular positions having reflections at the following 2 theta values: 7.35; 11.4; 13.69; 14.96; 17.49; 19.3 and 22.48 in each case ±0.2 degrees 2 theta.

2. The salt of formula (I) as claimed in claim 1, wherein the XRPD measured with CuKα radiation has reflections that are essentially identical to those shown in FIG. 1.

3. The salt of formula (I) as claimed in claim 1, wherein the Raman spectrum has characteristic bands at the following wavelengths [cm$^{-1}$]: 2936; 1570; 1401; 1352; 998 and 856, in each case ±2 cm$^{-1}$.

4. A method for the production of the salt as claimed in claim 1, the method comprising:
dissolving naphthalene-1,5-disulfonic acid in a solvent A;
adding a solution of (R)-3-(6-aminopyridin-3-yl)-2-(1-cyclohexyl-1H-imidazol-4-yl)propionic acid ethyl ester in a solvent B;
obtaining the naphthalene-1,5-disulfonic acid salt of (R)-3-(6-aminopyridin-3-yl)-2-(1-cyclohexyl-1H-imidazol-4-yl)propionic acid ethyl ester of formula (I); and
optionally partially or completely removing the solvents.

5. The method of claim 4, wherein the solvents A and B are the same or different, and are selected from the group consisting of ethanol, acetone, methyl ethyl ketone, acetonitrile, tetrahydrofuran, dimethyl sulfoxide, dimethylformamide, N-methylpyrrolidinone, methanol, propanol, butanol and water.

6. A pharmaceutical composition comprising a salt as claimed in claim 1 and a pharmaceutically suitable and physiologically compatible carrier substance, additive and/or auxiliary.

7. The salt of formula (I) as claimed in claim 2, wherein the Raman spectrum has characteristic bands at the following wavelengths [cm$^{-1}$]: 2936; 1570; 1401; 1352; 998 and 856, in each case ±2 cm$^{-1}$.

8. A pharmaceutical composition comprising a salt as claimed in claim 2 and a pharmaceutically suitable and physiologically compatible carrier substance, additive and/or auxiliary.

9. A pharmaceutical composition comprising a salt as claimed in claim 3 and a pharmaceutically suitable and physiologically compatible carrier substance, additive and/or auxiliary.

10. A pharmaceutical composition comprising a salt as claimed in claim 7 and a pharmaceutically suitable and physiologically compatible carrier substance, additive and/or auxiliary.

* * * * *